United States Patent [19]

Guth

[11] 4,407,152
[45] Oct. 4, 1983

[54] BREATH TEST SIMULATOR AND METHOD

[76] Inventor: Richard U. Guth, 439 N. 46th St., Harrisburg, Pa. 17111

[21] Appl. No.: 312,766

[22] Filed: Oct. 19, 1981

[51] Int. Cl.³ ............................................. G01N 31/00
[52] U.S. Cl. ...................................... 73/1 G; 261/124
[58] Field of Search ........................ 73/1 G, 1 R, 23; 128/719; 261/124

[56] References Cited

U.S. PATENT DOCUMENTS

| | | | |
|---|---|---|---|
| 3,854,319 | 12/1974 | Burroughs et al. | 73/1 G |
| 3,885,414 | 5/1975 | Reville | 73/1 G |
| 3,943,604 | 4/1976 | Hoppesch | 73/1 G |
| 4,003,240 | 1/1977 | Durbin | 73/1 G |
| 4,140,735 | 2/1979 | Schumacher | 261/124 |

FOREIGN PATENT DOCUMENTS 534724 11/1976 U.S.S.R.

OTHER PUBLICATIONS

Bulletin No. S69, Luckey Laboratories, Inc.

Flyer for Mark IIA Alcohol Breath Simulator, Smith & Wesson.

Dubowski, Breath-Alcohol Simulators: Scientific Basis and Actual Performance, Journal of Analytical Toxicology, vol. 3, Sep./Oct. '79, pp. 177–182.

Primary Examiner—Stephen A. Kreitman
Attorney, Agent, or Firm—Thomas Hooker

[57] ABSTRACT

A breath test simulator and method for accurately calibrating breath test instruments used to determine the concentration of ethyl alcohol in breath. The simulator includes concentric chambers filled with a known concentration of ethyl alcohol-water solution. Air flowed into the first chamber is bubbled up through the solution in that chamber, sputtered through openings formed in the wall separating the chambers, bubbled up through the solution of the second chamber and is flowed thence to the breath test instrument. The air pressure and temperature of the solutions are accurately controlled to assure the effluent precisely simulates human breath leaving a precisely known alcohol vapor concentration.

31 Claims, 6 Drawing Figures

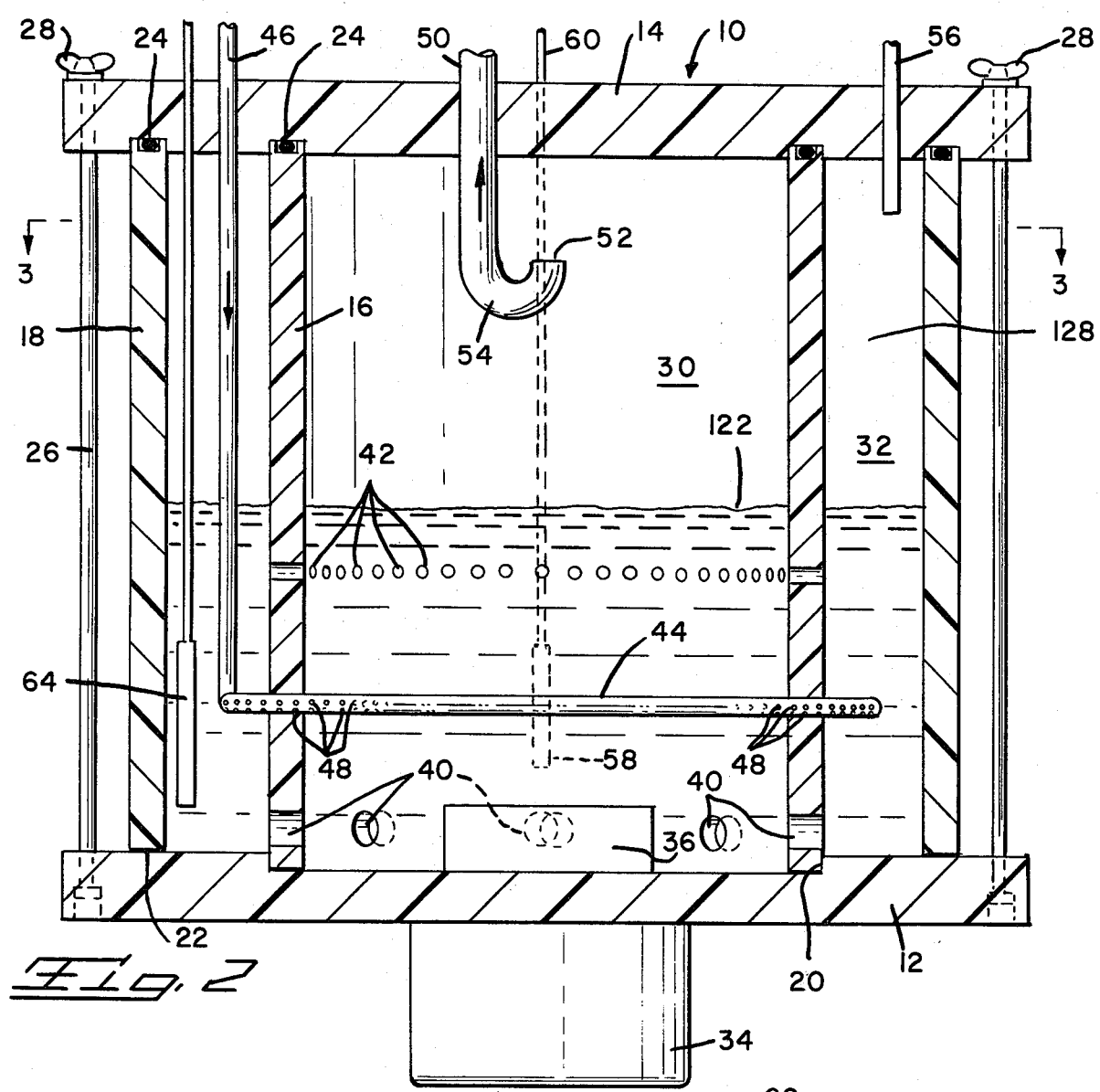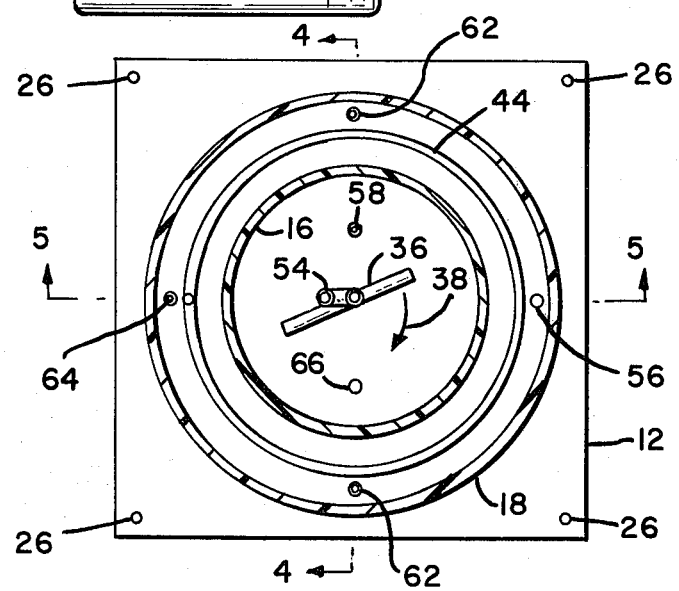

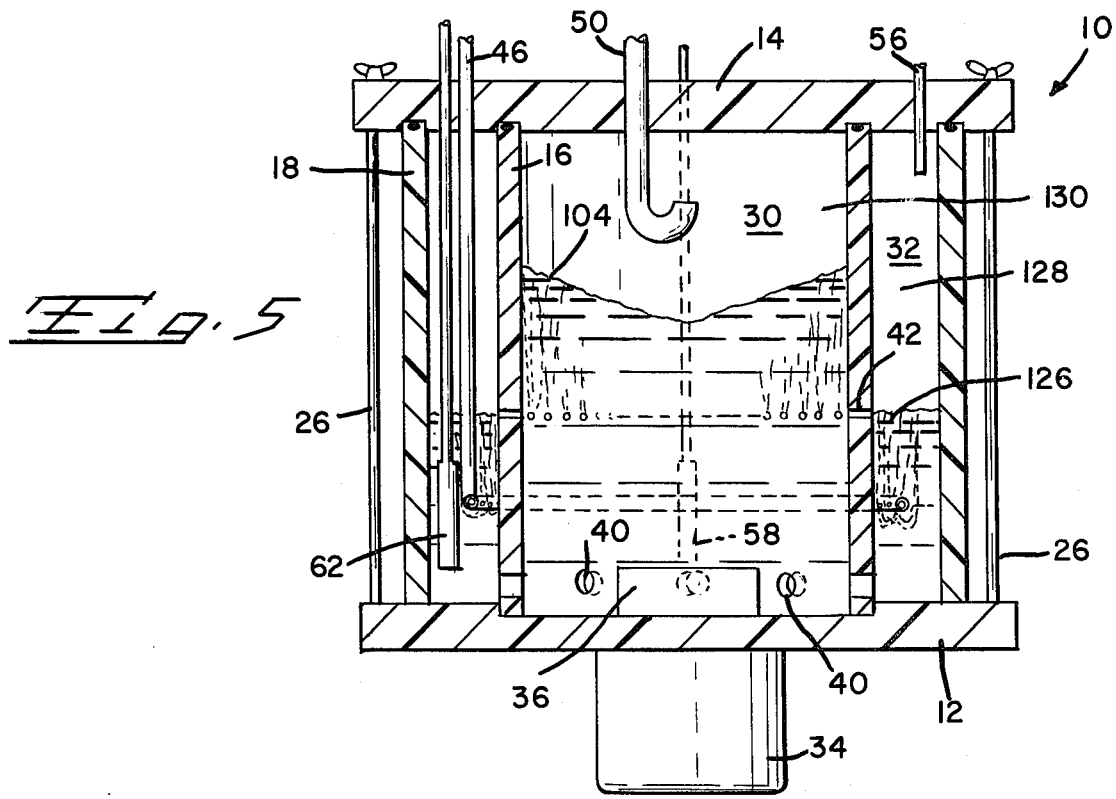
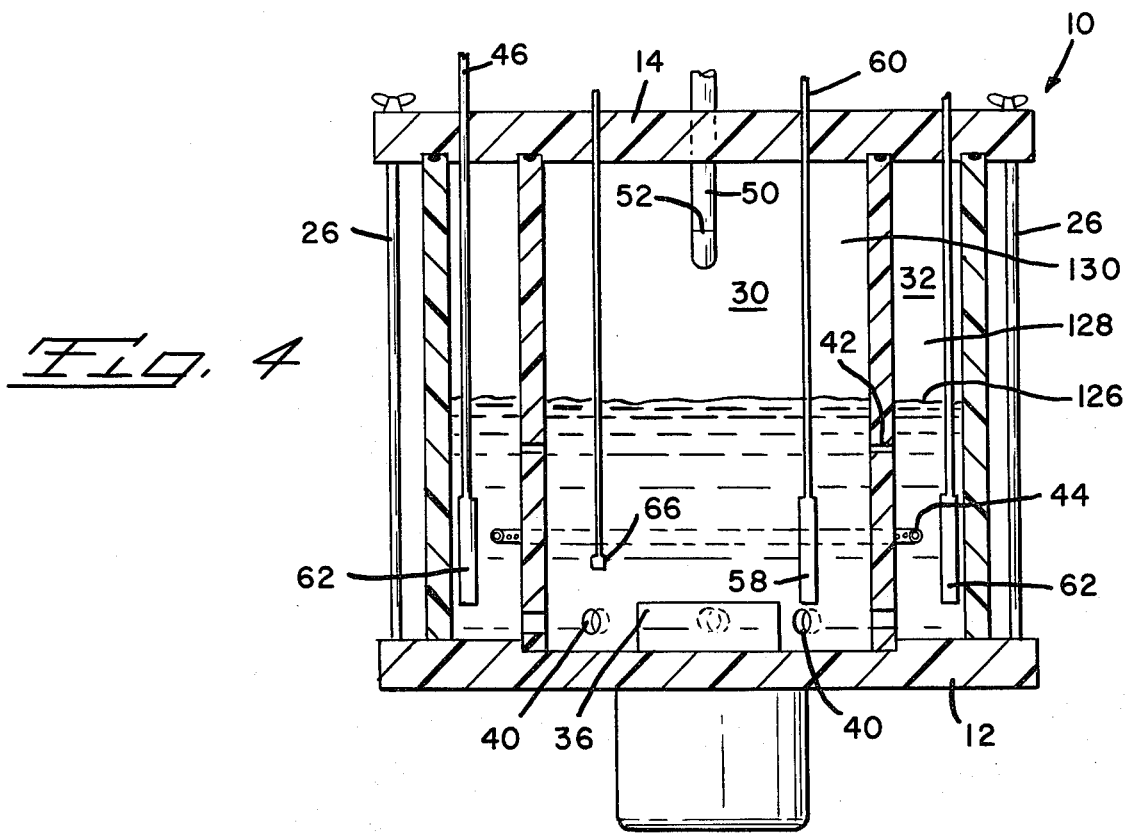

BREATH TEST SIMULATOR AND METHOD

The invention relates to apparatus and methods for supplying a breath test instrument with an effluent having a precisely controlled concentration of ethyl alcohol. The effluent is used to calibrate breath test instruments prior to conducting a breath test to determine the concentration of alcohol in the breath of a subject and indirectly, the amount of alcohol in the subject's blood. Breath tests are commonly used to determine whether the subject has violated a drunk driving law.

The accuracy of the breath test is directly dependent upon how accurately the machine is calibrated and the calibration test is only as accurate as the alcohol vapor concentration in the effluent supplied by the simulator. The simulator of the present invention flows air through an alcohol-water solution of given concentration and controlled temperature to provide a discharge effluent having a precisely controlled alcohol concentration. Repeated operation of the simulator will produce an effluent with the same alcohol concentration provided the alcohol in the solution is not depleted. By assuring that the effluent has a constant known alcohol concentration, the instrument is calibrated accurately and subsequent breath tests accurately measure the blood alcohol concentration of the subject.

At present, breath test instruments are calibrated using breath test simulators having a single glass chamber for the alcohol-water solution and an attached top with dependent mercury column thermometer, heating element, bubbler tube and paddle wheel stirrer. In most cases, a manual squeeze bulb is used to flow ambient air to the bubbler tube. The air bubbles up through the 500 ml. alcohol water solution within the chamber and into the head space from which it is flowed to the breath test instrument. In some cases, an air pump may be used to flow a continuous discharge through the simulator and to the instrument. Conventional simulators of the type described are manufactured by Luckey Laboratories, Inc. of San Bernardino, Calif.

Conventionally, breath test instruments used to determine blood alcohol concentrations are calibrated on the assumption that the simulator is a precision instrument and reliably and repeatedly provides an effluent having a known alcohol vapor concentration. In the field, there is no way of checking whether or not the simulator effluent alcohol concentration is correct.

An analysis of the conventional breath test simulator and its mode of operation concludes that the alcohol concentration in the effluent unpredictably varies sufficiently so that there is no assurance that a breath test instrument can be calibrated accurately using the effluent. As a result, any subsequent breath test performed by the instrument is inaccurate. The inherent inaccuracy of the simulator renders the breath test inaccurate. See, Dubowski, Breath-Alcohol Simulators: Scientific Basis and Actual Performance, Vol. 3, Journal of Analytical Toxicology, September/October 1979, pp. 177–182.

All breath test simulators generate an alcohol vapor effluent by bubbling air through an ethyl alcohol-water solution. The alcohol concentration in the solution is determined in accordance with Henry's Law to result in a desired alcohol vapor concentration at a given temperature. Most breath tests are conducted to closely simulate exhaled human breath having a temperature of 34° C. with an alcohol concentration of 100 mg. per 210 liters. This concentration theoretically yields a reading of 0.100 on a properly calibrated breath test instrument to reflect the standard assumed breath alcohol concentration/blood alcohol concentration ratio of 2100:1.

As shown by Dubowski, the partition ratio for the ethyl alcohol-water solution is highly temperature dependent. Between 34° C. and 35° C., the partition coefficient increases by 6.8 percent per degree of temperature increase. This large temperature dependence of the alcohol vapor concentration means that slight variations in the temperature of the solution can markedly change the concentration of alcohol in the effluent. Measurements of the solution temperature in the conventional simulator set at an operating temperature of 34° C. indicate a true mean temperature of 34.16° C. with a range of 34.01° C. to 34.33° C. This temperature variation causes significant fluctuations in the effluent alcohol concentration and prevents accurate calibration of the breath test instrument.

The alcohol concentration in the discharge effluent of conventional breath test simulators may vary due to changes in the temperature of the head space above the water-alcohol solution. The alcohol concentration in the head space vapor may be increased due to radiation heating from the simulator cover. Additionally, the rapid pulsed flow of ambient air into the simulator tends to cool the solution in the conventional single chamber simulator and increases temperature variations in the solution.

Because of these and other problems inherent in conventional simulators, Dubowski concludes that they are not precision calibrating devices and should not be so used to calibrate breath test instruments.

The disclosed simulator is a precision instrument capable of accurately and repeatedly calibrating breath test instruments for precision measurement of breath alcohol concentration. The instrument includes two interconnected chambers filled with ethyl alcohol-water solution with one chamber surrounding the other chamber. The chambers are interconnected through openings in the bottom of the common wall so that stirring of the inner chamber flows solution into and out of the outer chamber to continuously agitate and intermix the solution in both chambers. The temperature of the solution in the inner chamber is very accurately controlled by a precision temperature sensor and resistive heating elements in the inner and outer chambers energized by a proportional controller. The temperature of the inner solution, as measured by the sensor, is maintained to 34 plus or minus 0.02° C., assuring that the effluent discharged from the head space above the inner chamber has a desired alcohol concentration of plus or minus 0.14 percent. The head space above the inner chamber is purged of collected vapor prior to a test to assure the vapor flowed to the instrument is not a uniform temperature.

The improved simulator includes an air filter, pump and regulator adjusted to deliver filtered ambient air to the outer chamber at a pressure of about 8 to 10 inches of water, closely simulating the pressure of normally exhaled human breath. This air is flowed into an annular dispersion ring located within the outer chamber below the rest surface of the solution and above the mixing holes communicating the chambers. The ring includes a series of fine holes so that the air is formed into small bubbles which rise up the solution and collect in the closed outer chamber head space. Further flow of air into the outer chamber head space increases the volume of the head space to force solution in the outer chamber into the inner chamber through the mixing holes and through a series of closely spaced diffusion holes formed around the circumference of the common wall above the ring. When the level of the solution in the outer chamber is lowered to the level of the diffusion holes, air is bubbled up through the remaining solution in the outer chamber and then is sputtered into the solution in the inner chamber and rises up this solution. The flow of solution from the outer chamber increases the solution volume of the inner chamber to increase the bubble rise distance. Rotation of the stirring bar forms a vortex in the inner chamber with solution being thrown outwardly and up against the common wall to increase the rise distance. The air sputtered into the inner chamber through the diffusion holes rises up through the actively swirling vortex to the inner chamber head space and is flowed to the instrument.

During the initial seconds of the breath test cycle, the vapor in the inner chamber head space is vented to the atmosphere to assure that the solution supplied to the breath test instrument is at the desired temperature. The flow of solution into the inner chamber during startup aids in ejecting the original head space vapor.

The stir bar assures that the solution in the outer chamber is actively mixed with the solution in the inner chamber and maintained at approximately 34° C. Heaters are provided in the outer chamber to compensate for heat loss through the exterior walls. The outer chamber effectively insulates the inner chamber from the heat loss through the common wall.

As the air is bubbled through the outer chamber, sputtered through the common wall into the inner chamber and bubbled up through the actively swirling vortex in the inner chamber, it is heated to the temperature of the solution and acquires an equilibrium concentration of alcohol vapor. The solution in the inner chamber is accurately maintained at 34° plus or minus 0.02° C. to assure that when the air enters the inner chamber head space it is essentially exactly at the desired temperature and, according to Henry's Law, contains the desired alcohol concentration dependent upon the concentration of alcohol in the solution. While in practice, the temperature of the solution in the outer chamber may vary slightly from the temperature of the solution in the inner chamber, the sputtering of the air into the inner chamber and the bubbling up through the actively swirling inner chamber vortex assure that the head space vapor is maintained at the desired temperature.

During startup of the simulator, nonproportional boost heaters are powered until the temperature of the solution nears the desired temperature. These heaters are then deactivated so that the temperature of the solution is more slowly raised by the proportionally controlled heaters to the desired operating temperature. In this way, the simulator may be heated to the operating temperature in as little as 5 minutes.

The two-chamber simulator uses a one-liter charge of alcohol-water solution with about one-half liter of solution in each compartment. In contrast, the conventional simulator uses 500 ml. of solution. The use of a larger total volume of solution means that the concentration of alcohol in the solution is depleted more slowly per test than the concentration in the conventional simulator. In calibration tests requiring equal volumes of effluent, the solution in the present simulator will be depleted of alcohol twice as slowly as the solution in conventional simulators and will have to be replaced one-half as often.

In the disclosed simulator, the common wall between the inner and outer chambers is sandwiched between the base and cover plate and the inlet pipe, outlet pipe, heaters and sensor are carried by the cover plate. This means that the chambers are easily cleaned by removing the cover plate and freely lifting the separating or inner wall from the base plate. The remaining outer wall and plates are then easily cleaned without having to reach into the narrow outer chamber.

Other objects and features of the invention will become apparent as the description proceeds, especially when taken in conjunction with the accompanying drawings illustrating the invention, of which there are three sheets and one embodiment.

IN THE DRAWINGS

FIG. 2 is a vertical sectional view taken through the simulator;

FIG. 3 is a sectional view taken along line 3—3 of FIG. 2;

FIG. 4 is a sectional view taken along line 4—4 of FIG. 3;

FIG. 5 is a view taken along line 5—5 of FIG. 3 during operation of the simulator.

DESCRIPTION OF THE INVENTION

Figure 1:
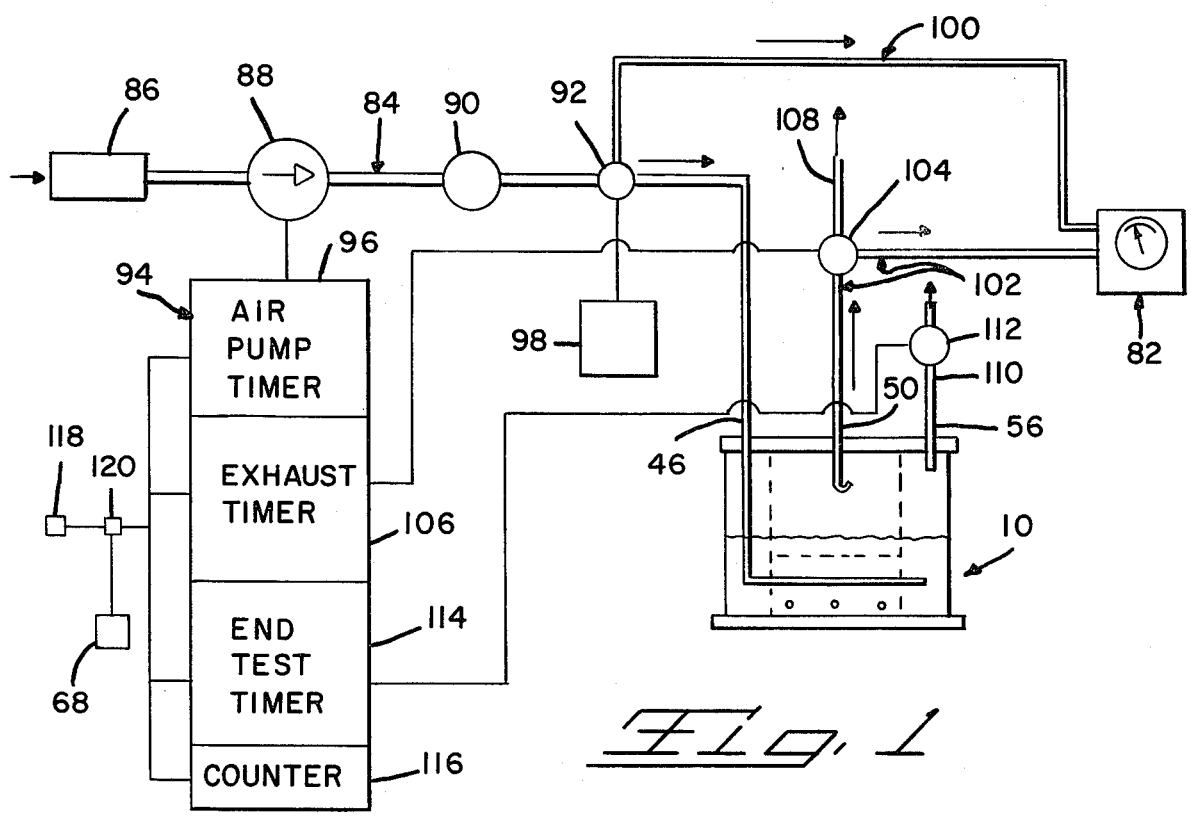
FIG. 1 illustrates the simulator, its controls and various lines connecting the simulator to a breath test instrument.

Breath test simulator 10, shown in FIGS. 2 through 5, includes a rectangular base plate 12, removable rectangular cover plate 14 and inner and outer concentric cylinders 16 and 18. The lower end of the inner cylinder fits loosely a round recess 20 formed in the upper surface of plate 12. The bottom of the outer cylinder is sealed to the base plate at joint 22. The upper ends of cylinders 14 and 16 are at the same level, each including a central groove with O rings 24 fitted therein for forming fluid and gas-tight seals with the flat lower surface of cover plate. The cylinders 16 and 18 are held between plates 12 and 14 by four clamp bolts 26. The clamp bolts extend through the corners of the base and cover plates and include heads engaging the lower corners and wing nuts 28 engaging the cover plate. Tightening down of the wing nuts holds the two cylinders in position as shown in FIG. 2 to form an inner cylindrical chamber 30 defined by the inner wall of inner cylinder 16 and the adjacent portions of the inner walls of the base and cover plates and an outer hollow cylindrical chamber 32 defined by the outer surface of cylinder 16, the inner surface of cylinder 18 and the adjacent surfaces of the base and cover plates. Chambers 30 and 32 have approximately the same volume.

The inner and outer cylinders 16 and 18 may be formed of transparent material, such as Lucite plastic although other materials may be used if desired. The base and cover plates may be formed of plastic or aluminum. The base plate is formed from a non-magnetic material because of the magnetic stirrer used to agitate the contents of chambers 30 and 32. If desired, the outer surfaces of the simulator may be insulated.

A conventional magnetic stirrer motor 34 is secured to the lower surface of base plate 12 in the center of inner cylinder 16 and a magnetic stirrer bar 36 is positioned on the bottom of recess 120 over the motor 34 such that actuation of the motor 34 rotates the stirrer bar in the direction of arrow 38 shown in FIG. 3.

Eight spaced solution mixing holes 40 are extend through the bottom of inner cylinder 16 slightly above the upper surface of base plate 12. The holes 40 are formed at an angle of approximately 45 degrees to a radius extending through the center of the inner end of each hole with the inner end of each hole located counterclockwise of the outer end of the hole when the cylinder is viewed from the top. In this way, solution in the inner chamber is rotated clockwise by the mixing bar 36 and is forced through the angled mixing holes and flows into the solution in chamber 32. The flow from the inner chamber to the outer chamber is in response to the passage of the ends of the stirrer bar 36. The solution flows back from the outer chamber to the inner chamber after passage of the ends.

A series of closely spaced radial secondary diffusion holes 42 extend through the inner cylinder 16 in a ring with adjacent holes 42 spaced apart approximately three times the diameter of individual holes. The holes 42 are located in the middle of cylinder 16 between plates 12 and 14.

In a breath test simulator 10 having a total solution volume of approximately 1 liter, the inner chamber 30 may have a diameter of slightly less than four inches and the outer chamber may have a diameter of slightly less than 6 inches. Holes 40 may be about ¼ inch in diameter and holes 42 may be approximately 1/16 inch in diameter and spaced apart, diameter to diameter, by approximately 3/16 inch. The row of holes 42 may be about 2 inches above the base plate 12. The height of the outer cylinder 18 is about 5 inches.

Circular hollow air dispersion ring 44 is located in the center of outer chamber 32 approximately midway between the inner and outer cylinders and at a level about midway between the diffusion holes 42 and mixing holes 40. Ring 44 is connected to and supported by an air inlet pipe 46 which extends through cover plate 14 and down the outer chamber to the ring. Circumferential rows of small bubble holes 48 are formed through the inside, outside and bottom of the dispersion ring so that air flowing through the inlet pipe 46 to the ring is flowed into the solution in the inner chamber in the form of a large number of fine bubbles.

Effluent outlet pipe 50 extends through simulator top plate 14 into chamber 30 with an inlet end 52 located on the axis of the concentric cylinders 16 and 18 and facing upwardly toward the top plate. The end is connected to the remainder of the pipe by a reverse bend 54. An exhaust pipe 56 extends through cover plate 14 to the top of the outer chamber 32.

Electric resistance heater 58 is immersed in the solution in inner chamber 30 and is supported in the chamber on a rigid shaft 60 extending through the cover plate 14. Shaft 60 carries the power leads for heater 58. A pair of like resistance heaters 62 extend into the solution in the outer chamber 32 on diametrically opposite sides of the chamber. Another resistance heater 64 extends into the solution in chamber 32 between the heaters 62. Heaters 62 and 64 are supported on the cover plate 14 similarly to heater 58. All the heaters have a 65-watt output when fully powered. An accurate resistive temperature sensor 66 is supported on the upper plate 14 and extends into the solution in the inner chamber 30 across from the heater 58. The ends of the heater 58 and sensor 56 are above the path swept by magnetic stirrer bar 36.

The temperature of the solution in chambers 30 and 32 is accurately monitored and controlled by electric temperature control 68. When the simulator 10 is used in calibrating breath test instruments, the temperature of the water-alcohol solution should be maintained at exactly breath temperature, 34° C. The control assures that the solution in simulator 10 is initially rapidly heated to a temperature slightly below the desired temperature, is then heated to the desired 34° C., and is accurately maintained at the desired 34.00 temperature with a variation as small as 0.02° C., as measured by sensor 66. Insulation surrounding the simulator may be used to help maintain the temperature accurately, particularly where the ambient temperature is low.

The control 68 includes a digital temperature readout 70 which reads the temperature sensed by sensor 66. A control line for warm-up heater 64 includes a temperature boost power source 72 and a non-proportional on/off controller 74 for source 72. During warmup of the simulator, controller 74 actuates source 72 to energize heater 64 until the temperature sensed by sensor 66 is slightly less than desired operating temperature for the solution. In the case of a 34° operating temperature, the cutoff temperature for controller 74 may be 32.5° C.

A control line for heaters 58 and 62 includes a proportional triactor power source 76 and a proportional controller 78 for actuating the triactor power source. When the simulator is used in calibrating breath tests at an operating temperature of 34°, the set points for the proportional controller 78 may be as small as 34 plus or minus 0.02° C.

The on time of controller 78 is determined on a time base by the deviation of the sensed temperature from the desired or set point temperature. As the set point temperature is approached during warm-up, the heaters 58 and 62 are alternatively energized and de-energized. The length of each period when the heaters are de-energized or off is predetermined by a setting in control 68. The length of each on time interval is variable, depending upon the difference between the temperature sensed by sensor 66 and the desired operating temperature, the heating elements are energized for progressively shorter intervals of time until the sensed temperature reaches the operating temperature. Then, the heaters are deactivated until the sensed temperature falls below the operating temperature set point. When the simulator is at the operating temperature of 34° C., the observed temperature is controlled to 34 plus or minus 0.02° C.

The energy supplied to the heaters when power source 76 is on is internally adjustable in control 68 as is the cycle rate for controller 78. For example, the cycle rate may vary from 2.4 seconds down to 0.150 second. Shorter cycle rates are preferred for accurate temperature control. The triactor of power source 76 is preferably zero-fired for full power line cycles. This effectively eliminates radio frequency interference noise and half-waving of the alternating current voltage.

Control 68 includes an internal calibration source 80 which is preferably adjusted to a National Bureau of Standards reference for assured accuracy. The source has the properties of sensor 66 at the desired operating temperature, in the case of breath test analysis, 34.00° C. The control 68 includes a switch for substituting source 80 for sensor 66. When this is done, readout 70 should read 34.00° C. exactly. Any other readout is an indication of circuitry malfunction. The operator may check the circuitry of control 68 at any time by substituting source 80 for sensor 66.

FIG. 1 illustrates the breath test simulator 10, a breath test instrument 82 and the various controls and lines used in conjunction with simulator 10 for conducting a simulated breath test to calibrate the instrument. Air inlet line 84 includes a replaceable charcoal filter 86 on its free end, an air pump 88, pressure regulator 90 and normally open solenoid controlled valve 92 located in the line between the regulator and simulator air inlet pipe 46. Regulator 90 controls the simulator inlet air pressure and is usually set at 8 to 10 inches of water to simulate the pressure of human breath.

Main control 94 includes an air pump timer 96 operable to actuate pump 88 during a cycle of operation of the simulator 10. Manually operated switch 98 shifts valve 92 so that filtered air from the pump bypasses simulator 10 and flows directly to the breath test instrument through line 100 for an air blank test. During an air blank test, line 100 is connected to the inlet pipe of instrument 82. Air outlet line 102 extends from the simulator outlet pipe 50 through normally open solenoid control valve 104 to the inlet pipe of breath test instrument 82. The main control 94 also includes an exhaust timer 106 which, when actuated, shifts valve 104 so that the flow through outlet pipe 50 is directed to atmosphere through vent 108.

The simulator exhaust pipe 56 is connected to a level-return line 110 carrying the solenoid control valve 112 and having a discharge end open to atmosphere. The valve 112 is controlled by an end test timer 114 in main control 94 such that when the valve 112 is opened, gases in the outer chamber 32 are vented to atmosphere. The main control 94 also includes a digital counter 116 which provides a numerical indication of the number of tests run using a single charge of alcohol-water solution in simulator 10.

Simulated breath tests are run for calibrating breath test instruments automatically upon actuation of a single initiaion switch 118. Tests should not be run until the electric temperature control 68 has heated the solution in simulator 10 to the desired operating temperature. To this end, a cutout switch 120 may be provided between switch 118 and main control 94 isolating the two until the solution within the simulator is heated to the desired temperature level and appropriate circuitry closes switch 120.

OPERATION OF THE BREATH TEST SIMULATOR

Prior to conducting a simulated breath test to calibrate a breath test instrument, the operator checks to determine whether the alcohol-water soluition in the simulator is sufficiently depleted of alcohol to jeopardize the accuracy of the calibration. If so, the solution must be replaced with a fresh solution having the required alcohol concentration. The solution is changed by releasing wing nuts 28 and removing the cover plate 14 and the various heaters, sensors and pipes supported by the cover plate from within the chambers. The cover plate and its supported elements are then carefully cleaned and rinsed. Upon removal of the cover plate, the inner cylinder 16 and stir bar 36 are freely lifted from recess 20 and washed and cleaned. The water-alcohol solution within the sumulator is discarded and the chamber is thoroughly cleaned and rinsed. Removal of the inner cylinder 16 from the base plate 12 makes it an easy matter to clean the interior of the simulator.

Following cleaning of the various simulator parts, the simulator is reassembled and filled with a volume of a specially prepared ethyl alcohol-water solution having a precisely known concentration of alcohol per unit volume of water. The alcohol-water solution may have 1.21 grams of alcohol per liter of water to produce an effluent having a concentration of 0.100 grams of alcohol vapor per 210 liters of air at 34° C. This concentration of alcohol solution is conventionally used in breath test simulators to calibrate breath test instruments to a reading of "0.100", corresponding to an assumed blood-alcohol concentration breath-alcohol concentration ratio of 2100:1. The inner chambers of simulator 10 are filled with one liter of the alcohol-water solution. Once equalized between the inner and outer chambers 30 and 32, the solution has a level 122 slightly above the circumferential row of secondary air diffusion holes 42 in the inner cylinder 15.

Figure 6:
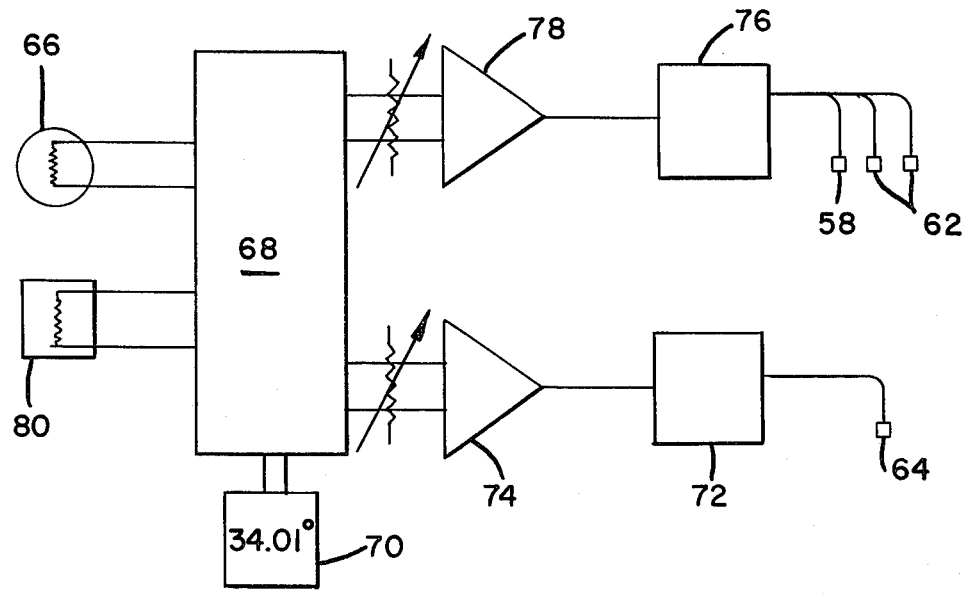
FIG. 6 is a representational view of the electric temperature control system used to maintain the solution within the simulator at an operating temperature.

The simulator 10 is connected to the heating and control circuitry shown in FIGS. 1 and 6, counter 116 is zeroed and motor 34 is turned on. The electric temperature control is turned on to heat the solution within the simulator to the desired 34° C. operating temperature. Normally when the control is turned on, the temperature of the solution within the simulator is considerably lower than the 32.5° C. set point for the nonproportional 74 controller for heater 64 so that all four heaters 58, 62 and 64 are energized to rapidly heat the solution. When the solution reaches the set point for controller 74, heater 64 is de-energized and the remaining heating of the solution is accomplished by heaters 58 and 62 controlled by the proportional controller 78 in a manner previously described. The use of heater 64 enables the solution to be rapidly brought up to temperature. After the heater 64 is deactivated the proportionally controlled heaters 58 and 62 are used through the more accurate controller 78 to bring the solution to the very accurately controlled operating temperature of 34 plus-or-minus 0.02° C.

During heating of the solution and operation of the simulator that the stirrer bar 36 rotates on the surface of recess 20 in the direction of arrow 54. Rotation of the stirrer motor actively rotates the solution within the inner chamber 30 to assure the solution is maintained at a uniform temperature. The rotation of the stirrer bar 36 forces solution at the bottom of the inner chamber into the outer chamber through the angled solution mixing holes 40. After the ends of the bar pass adjacent holes to force solution in the outer chamber, solution flows back into the inner chamber through the same holes. In this way, there is active intermixing of the heated solution between the inner and outer chambers. The actively rotating solution within the inner chamber 30 is thrown out and up against the inner cylinder 16 to form vortex 104.

Since sensor 66 measures the temperature of the solution in the inner chamber, the outer chamber solution is less actively stirred than the inner chamber solution and the outer chamber includes a large surface area outer wall, the temperature of the solution in the outer chamber may be slightly cooler than the temperature of the solution in the inner chamber.

When the operator observes the temperature of the solution as indicated on readout 70 has stabilized at desired operating range and cutout switch 120 has been closed, a breath simulation test may be initiated by actuating the test switch 118. Prior to actuating the switch, the manually controlled valve 92 is in its normal position communicating the regulator 90 with air inlet pipe 46. Solenoid controlled valve 104 is in its normal position communicating outlet pipe 50 with breath test instrument 82 and solenoid controlled valve 112 is in its normal closed position. When switch 118 is actuated, air pump 88 is powered to draw air through filter 86 into the line 84 and flow the air through regulator 90, valve 92 and into the air inlet pipe 46 and, ultimately, to the dispersion ring 44 immersed within the alcohol-water solution within the outer chamber 32. The filter 86 removes solids and undesirable gases from the air pumped to the simulator. Regulator 90 is adjusted to control the pressure of the output to simulate the pressure of exhaled human breath.

The air flowing down inlet pipe 36 and into ring 44 bubbles out holes 48 into the solution in the outer chamber and rises up through the solution, past the secondary diffusion holes 42 to the outer chamber head space 106 located above the solution. The air flow forms a dense bubble cloud distributed throughout the solution in the outer chamber above the ring 44. Some bubbles are initially forced below the ring but rapidly rise to the outer chamber head space 128 with the rest of the flow. The ring 44 is positioned approximately 1 inch above the top of bores 40 to assure that the bubbles are not drawn into the inner chamber 30 through the bores 40.

The air flowing from ring 44 is initially collected in head space 128 so that the volume of air in the head space 128 is increased, increasing the pressure in the head space and correspondingly lowering the level of the solution in the outer chamber from level 122 shown in FIG. 2 until the solution reaches level 126 shown in FIG. 5 at the circumferential row of secondary diffusion holes 42 in the inner cylinder 16. When the solution in the outer chamber is lowered to level 126, additional air flowing into head space 128 is sputtered through the diffusion holes 42 and into the swirling solution in inner chamber 36. These bubbles flow upwardly through the inner chamber, break through the surface of vortex 104 and collect in the inner chamber head space 130. Air from head space 130 flows through the inlet 52 and through outlet pipe 50 to valve 104.

During the first five seconds of each cycle of operation in simulator 10, timer 106 shifts valve 104 to vent vapor discharged from head space 30 to atmosphere through line 108. The reverse bend 54 in outlet pipe 50 reduces the probability that solution droplets are drawn into the outlet pipe together with the effluent.

The enlargement of head space 128 by the upward flow of bubbles from ring 44 forces the solution in the outer chamber into the inner chamber through the holes 40 and 42. Thus, as illustrated in FIG. 5, the volume of solution in the inner chamber is increased to increase the height of the solution or column for the bubbles flowing into the inner chamber through the secondary diffusion holes 42. The height of solution of the column above the holes 42 is increased by the swirling of the solution which throws the solution up on the cylinder 16 with formation of vortex 104 and an increase of the height or column of solution above holes 42. The gas flowing through holes 42 prevents the solution in the inner chamber from flowing into the lower level outer chamber.

After the initial five second venting of the head space 130, simulator 10 flows effluent to the breath test instrument 82. The operator may then calibrate the instrument according to its particular procedures. Control 94 is adjusted so that end test timer 114 ends the test run only after a sufficient volume of effluent has been flowed to instrument 82 to meet the requirements of the instrument.

The effluent includes an air-alcohol vapor-water vapor mixture in equilibration with the alcohol-water solution within the simulator. The vapor-solution equilibration is achieved by first passing the ambient temperature air through the agitated solution in the outer chamber 32, sputtering the gas through the secondary diffusion holes 42 and into the inner chamber and bubbling the gas through the solution column in the inner chamber. The resultant effluent closely simulates human breath and contains a precisely known correlation of alcohol vapor.

After the breath test instrument 82 has been supplied with sufficient effluent to complete the calibration breath test, timer 96 deactivates pump 88 and end test timer 114 is actuated to open valve 12 thereby venting the outer chamber head space 128 to atmosphere so that the solution in the outer chamber raises from level 126 to original level 122 and the level of the solution in the inner chamber lowers back to level 122. Counter 116 is actuated to indicate that the alcohol-water solution within the simulator has been used to conduct a breath test. Since each breath test removes alcohol from the solution, the concentration of the alcohol vapor in the effluent is progressively decreased with each successive test run using the same solution. Counter 116 counts each test run and is used to determine when it is necessary to replace the solution within the simulator in order to assure that the concentration of alcohol within the effluent is maintained within desired limits to assure that instrument 82 is accurately calibrated.

Following calibration of instrument 82, line 102 is disconnected from the instrument allowing air to flow through the line and back into the inner chamber head space 130. This retrograde flow through line 102 reduces condensation in the line. Condensation trapped in the line could adversely affect the accuracy of a subsequent calibration test.

Frequently in the calibration of breath tests instruments, it is desirable to run a "blank run", that is a test when the gas supplied to the instruments is known to be free of alcohol vapor. This type of test is used to assure that the instrument gives a proper reading in the absence of alcohol vapor and is free of alcohol. A "blank run" may be conducted using the FIG. 1 system by disconnecting the instrument end of line 102 from the instrument 82 and connecting the free end of line 100 to the instrument in its place. Switch 98 is tripped to connect line 84 to line 100 thereby flowing filtered, pressure regulated alcohol-free air directly from the regulator to the instrument. The pump 88 is then actuated for the desired time interval required by the particular instrument. At the end of the "blank run", valve 98 is deactuated and line 102 is reconnected to the instrument.

Simulator 10 has been described in connection with the generation of a precision effluent having a precisely controlled temperature and alcohol concentration for use in calibrating breath test instruments. The invention is not limited to such applications and, for instance, may be used to generate other types of precisely controlled alcohol vapor effluents for calibration or other uses or may be used to generate other precision effluents formed by bubbling a gas through a liquid. The liquid need not be aqueous.

While I have illustrated and described a preferred embodiment of my invention, it is understood that this is capable of modification, and I therefore do not wish to be limited to the precise details set forth, but desire to avail myself of such changes and alterations as fall within the purview of the following claims.

What I claim as my invention:

1. A breath test simulator including a first closed chamber, a second closed chamber surrounded by the first chamber with a common wall between the chambers, a series of diffusion holes extending through the wall to communicate the chambers and extending around the common wall at a level, a bubble generator in the first chamber surrounding the common wall at a level below the level of the diffusion holes, an outlet pipe opening into the top of the second chamber, a liquid temperature sensor in the second chamber, at least one liquid heater in each chamber, said sensor and heaters being located below the level of the diffusion holes, a temperature control for supplying energy to the heaters when the temperature sensed by the sensor is below a set point temperature, and means for moving liquid in the chambers to reduce temperature anomalies, whereby upon filling of the chambers with an ethyl alcohol solution to a level normally above the level of the dispersion holes, gas flowed through the bubble generator bubbles up through the liquid in the first chamber, collects in the top of the first chamber to eject liquid from the first chamber into the second chamber and increase the bubble column of liquid in a second chamber above the level of dispersion holes and to eject head space gases from the second chamber, sputters through the dispersion holes into the second chamber and bubbles up through the bubble column in the second chamber, so as to be brought into equilibrium with the liquid in the second chamber and assure the formation of an equilibrium concentration of ethyl alcohol vapor within the gas, and is flowed from the simulator through the outlet pipe.

2. A breath test simulator as in claim 1 wherein said common wall is cylindrical, the outer wall of the first chamber is cylindrical and the bubble generator comprises a circular bubbler tube.

3. A breath test simulator as in claim 2 including a series of openings communicating said chambers below the bubbler ring whereby said means for moving liquid moves liquid through said openings between said chambers.

4. A breath test simulator as in claim 3 wherein said openings extend through the bottom of said common wall and are arranged circumferentially around the common wall and wherein said means for moving liquid comprises a stirrer located within the second chamber adjacent said openings.

5. A breath test simulator as in claim 4 wherein said openings are angled in the direction of rotation of the stirrer to promote the flow of liquid from the inner chamber to the outer chamber.

6. A breath test simulator as in claim 1 wherein said heaters are resistance heaters and said temperature control includes a proportional controller for supplying an amount of electrical energy to the heaters proportional to the difference between the sensed temperature and the set point temperature.

7. A breath test simulator as in claim 6 including a pair of resistance heaters in the second chamber located on opposite sides of the first chamber.

8. A breath test simulator as in claim 1 including means operable to vent the outlet pipe to atmosphere during initial bubbling of gas through the simulator whereby the gas and liquid from the first chamber flowing into the second chamber vent second chamber head space gases to atmosphere.

9. A breath test simulator as in claim 8 including an exhaust pipe extending into the top of the first chamber and means operable to open the exhaust pipe to atmosphere following conducting a simulated breath test to allow liquid to return to the second chamber from the first chamber.

10. A breath test simulator as in claim 2 including a base plate, a cover plate, said outer and common walls being sandwiched between said plates, a permanent connection between the base plate and the outer wall, releasable seal connections between the cover plate and said outer and common walls and between the base plate and said common wall and means for releasably confining the walls between the base and cover plates.

11. A breath test simulator as in claim 10 wherein one of said plates includes means for releasably locating the common wall concentrically with the outer wall.

12. Apparatus for generating a saturated vapor effluent comprising a first closed chamber, a second closed chamber, a common wall between the chambers, a series of gas diffusion holes extending through the wall at one level to communicate the chambers, a bubble generator in the first chamber below the holes, a gas outlet pipe opening into the top of the second chamber above the level of the holes, and temperature control means for maintaining the temperature of liquid in the chambers at a working temperature within a close tolerance, whereby upon filling the chambers with a liquid having an evaporative constituent to a level normally above the holes, gas flowed through the bubble generator bubbles up through the liquid in the first chamber, sputters through the holes into the second chamber, bubbles up through the liquid in the second chamber, is brought into equilibrium with the liquid in the second chamber acquire a saturated constituent vapor concentration and is then flowed from the apparatus through the outlet pipe.

13. Apparatus as in claim 12 wherein said first chamber surrounds the second chamber, the common wall separates the chambers and said holes extend around the circumference of the common wall.

14. Apparatus as in claim 13 wherein said bubble generator includes a bubble ring surrounding the common wall.

15. Apparatus as in claim 14 including a stirring element located within the second chamber and an opening extending through the wall below the holes whereby the stirring element stirs the liquid within the inner chamber and flows liquid through said opening into and out of the first chamber.

16. Apparatus as in claim 13 wherein said common wall and the outer wall surrounding the first chamber are both cylindrical.

17. Apparatus as in claim 16 wherein said walls are confined between a base plate and a cover plate, a permanent seal between the bottom of the outer wall and the base plate, releasable seals between the tops of the common wall and outer wall and the cover plate, said base plate including means for releasably locating the common wall concentrically with the outer wall.

18. Apparatus as in claim 15 including a series of openings extending through the wall and around the circumference of the wall, said stirring element being located adjacent said openings and wherein said holes are all angled in one direction around the wall so that the stirring element flows liquid through the holes.

19. Apparatus as in claim 12 including at least one liquid heating element within each chamber, a temperature sensor located within the inner chamber and temperature control means for energizing the heating elements in response to the output of the temperature sensor.

20. Apparatus as in claim 19 wherein said temperature control means includes a proportional controller whereby the energy supplied to the heating elements is proportional to the difference between the temperature sensed by the sensor and a set point temperature.

21. In a simulator having two closed chambers and liquid in the chambers, the method of generating an effluent having a vapor in equilibrium with the liquid comprising the steps of:
   A. Controlling the temperature of the liquid in the chambers;
   B. Bubbling gas up through the liquid in a first chamber;
   C. Sputtering such gas from the first chamber through dispersion holes and into the liquid in the second chamber;
   D. Bubbling the gas in such second chamber up through the liquid in such chamber;
   E. Collecting the gas at the top of such second chamber; and
   F. During said bubbling and sputtering steps forming a vapor in such gas to bring such gas at the top of the second chamber in eqilibrium with the liquid in the second chamber.

22. The method of claim 21 including the step of swirling the liquid in the second chamber to form a vortex and increase the height of the bubble column.

23. The method of claim 21 including the step of flowing the liquid between the chambers to equalize the liquid temperature.

24. The method of claim 21 wherein the first chamber surrounds the second chamber and the chambers are separated by a common wall including the step of reducing heat loss from the second chamber liquid by flowing heat from the liquid in the second chamber through the wall and into the liquid in the first chamber.

25. The method of claim 21 including the step of venting the top of the first chamber to allow liquid to flow from the second chamber to the first chamber.

26. The method of claim 21 including the steps of first venting initial second chamber head space gas and initial second chamber bubbled gas and then flowing second chamber bubbled gas to an instrument.

27. The method of claim 21 including the steps of sensing the temperature of the liquid in the second chamber and supplying heat to both chambers in response to the difference between the sense chamber temperature and a set point temperature.

28. The method of claim 27 including the step of supplying energy to the liquid in the second chamber proportional to the difference between the sensed temperature and the set point temperature.

29. The method of claim 28 wherein the first chamber surrounds the second chamber and including the step of circulating liquid between both chambers around the circumference of the second chamber.

30. The method of claim 29 including the step of swirling the liquid in the second chamber to form vortex and increase the height of the bubble column.

31. The method of claim 21 including the step of collecting the bubbled gas in the first chamber to lower the level of the liquid in the chamber and flow part of the liquid into the second chamber to increase the bubble column of the second chamber.

* * * * *